United States Patent
Kang et al.

(10) Patent No.: US 10,394,013 B2
(45) Date of Patent: Aug. 27, 2019

(54) OPTIC ASSEMBLY AND LIGHT SOURCE DEVICE FOR ENDOSCOPE INCLUDING THE SAME

(71) Applicant: INTHESMART Inc., Seoul (KR)

(72) Inventors: Uk Kang, Seoul (KR); Ilhyung Shin, Jeju (KR)

(73) Assignee: INTHESMART Inc., Seoul (KR)

( * ) Notice: Subject to any disclaimer, the term of this patent is extended or adjusted under 35 U.S.C. 154(b) by 194 days.

(21) Appl. No.: 15/648,420

(22) Filed: Jul. 12, 2017

(65) Prior Publication Data

US 2018/0314055 A1  Nov. 1, 2018

(30) Foreign Application Priority Data

Apr. 26, 2017 (KR) .................. 10-2017-0053980

(51) Int. Cl.
*G02B 23/24* (2006.01)
*G02B 23/04* (2006.01)
*A61B 1/06* (2006.01)

(52) U.S. Cl.
CPC ......... *G02B 23/2461* (2013.01); *G02B 23/04* (2013.01); *G02B 23/2423* (2013.01); *G02B 23/2476* (2013.01); *A61B 1/0669* (2013.01); *A61B 1/0684* (2013.01); *G02B 23/2469* (2013.01)

(58) Field of Classification Search
CPC .............. G02B 23/04; G02B 23/2461; G02B 23/2476; A61B 1/0638; A61B 1/0661; A61B 1/0669
See application file for complete search history.

(56) References Cited

U.S. PATENT DOCUMENTS

| 4,273,431 A * | 6/1981 | Farmer | A61B 1/045 396/17 |
|---|---|---|---|
| 2002/0025119 A1* | 2/2002 | Otsuki | G02B 6/2817 385/47 |
| 2002/0109844 A1* | 8/2002 | Christel | B01J 19/0093 356/417 |
| 2013/0113911 A1* | 5/2013 | Hanano | G02B 21/16 348/79 |
| 2013/0335992 A1* | 12/2013 | Jaffe | F21V 11/00 362/552 |

* cited by examiner

*Primary Examiner* — Alexander K Garlen
(74) *Attorney, Agent, or Firm* — Patent Office of Dr. Chung Park

(57) ABSTRACT

Disclosed is an optical assembly including: an upper case which is provided with a first optical path for passing light from a first light source, and a second optical path, which communicates with a side of the first optical path and which introduces the light from a second light source into the first optical path; a lower case coupled with the upper case; and a beam splitter which is disposed in the first optical path, and which maintains a traveling direction with respect to the light from the first light source and changes a direction of the light from the second light source so that the light from the second light source can travel in the same direction as the light from the first light source.

6 Claims, 13 Drawing Sheets

[Fig. 1]
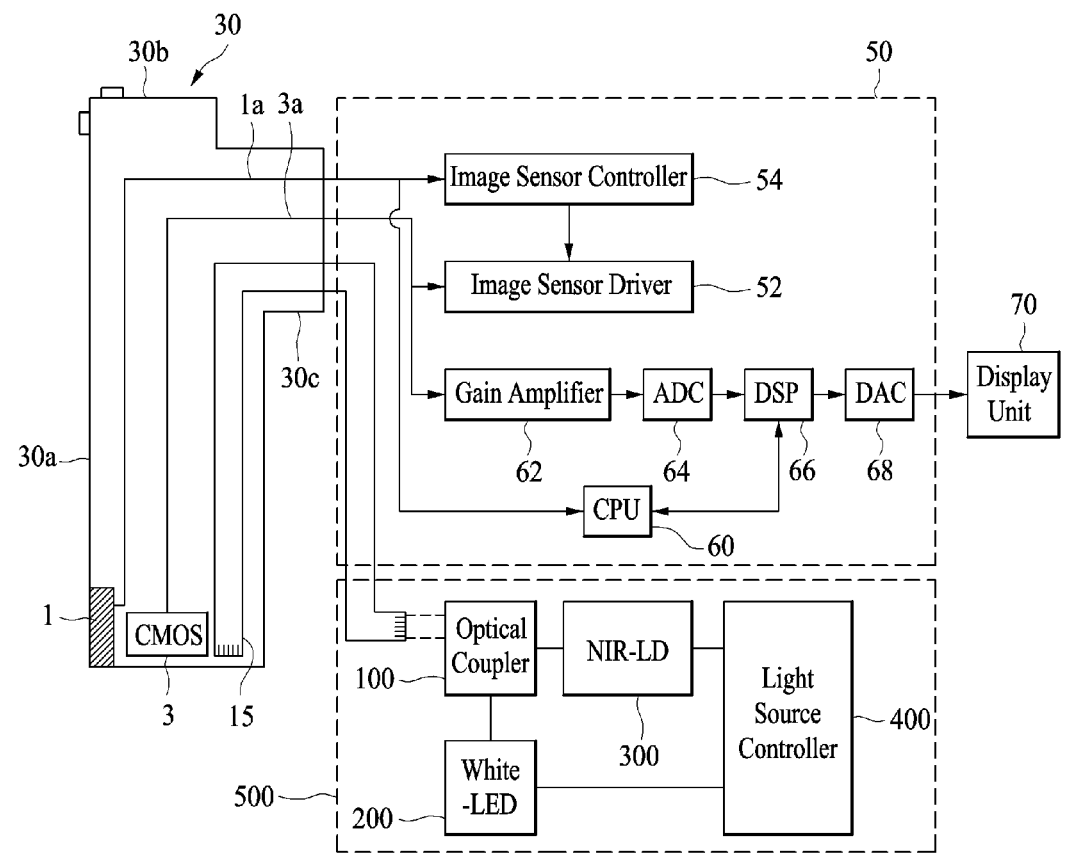

[Fig. 2]
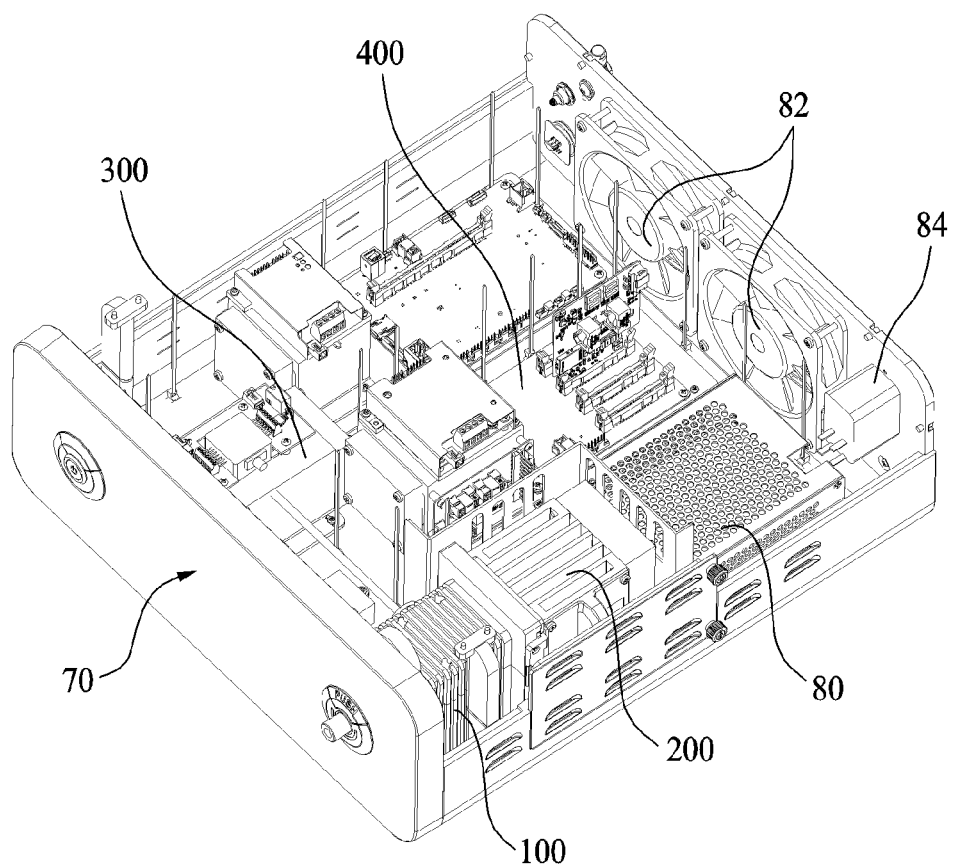

[Fig. 3]
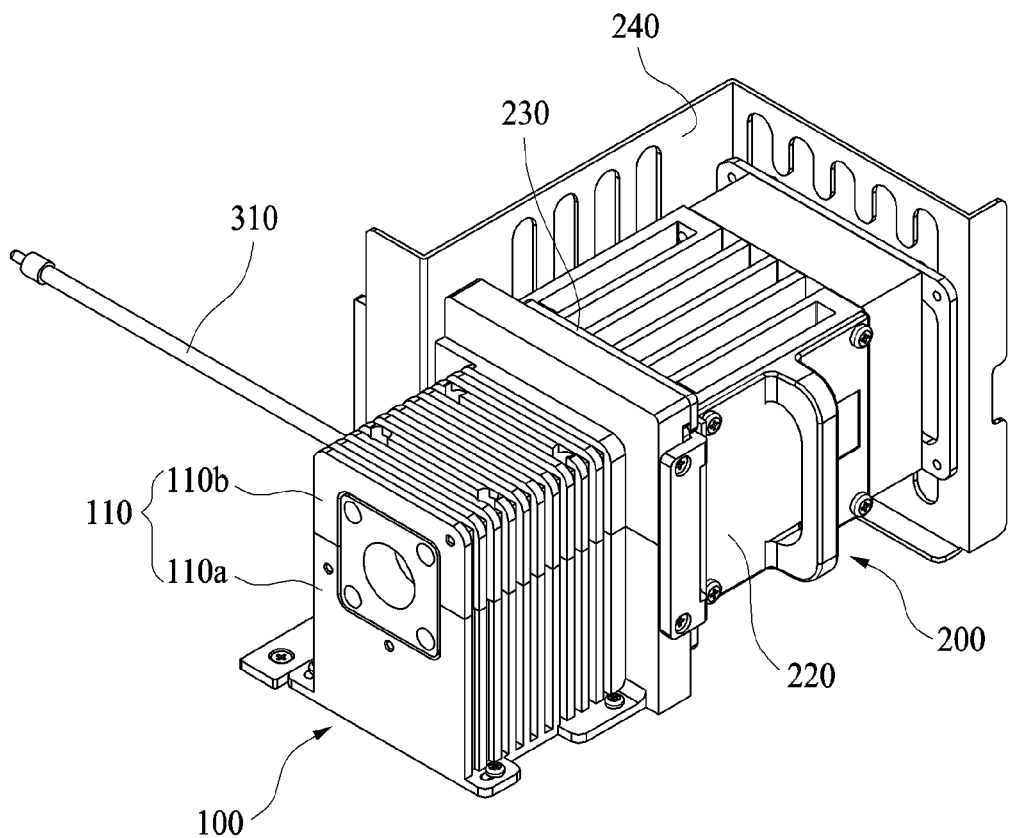

[Fig. 4]
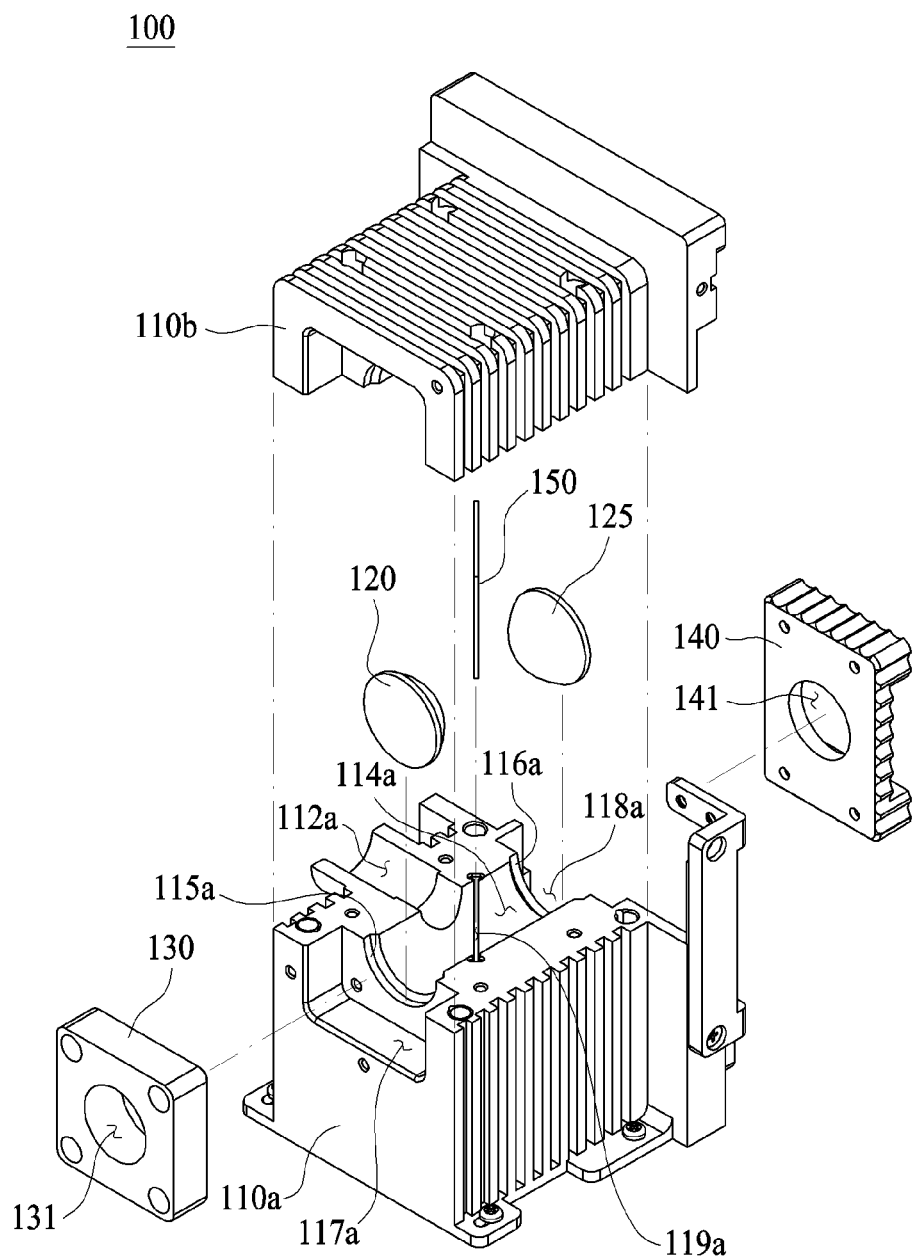

[Fig. 5]
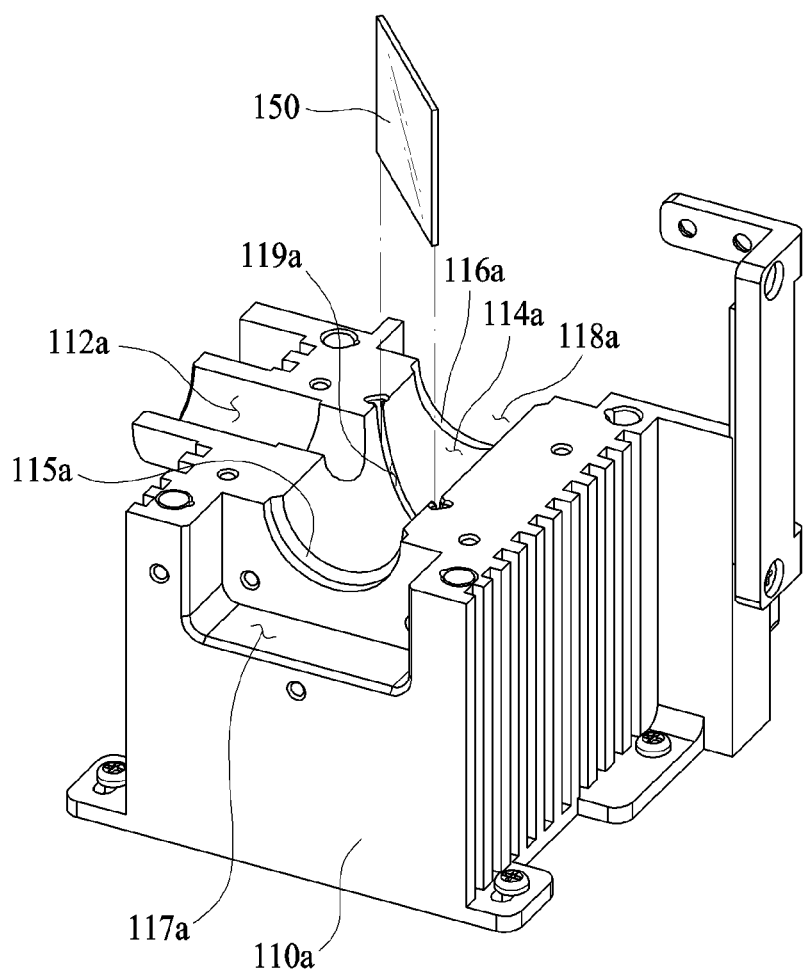

[Fig. 6]
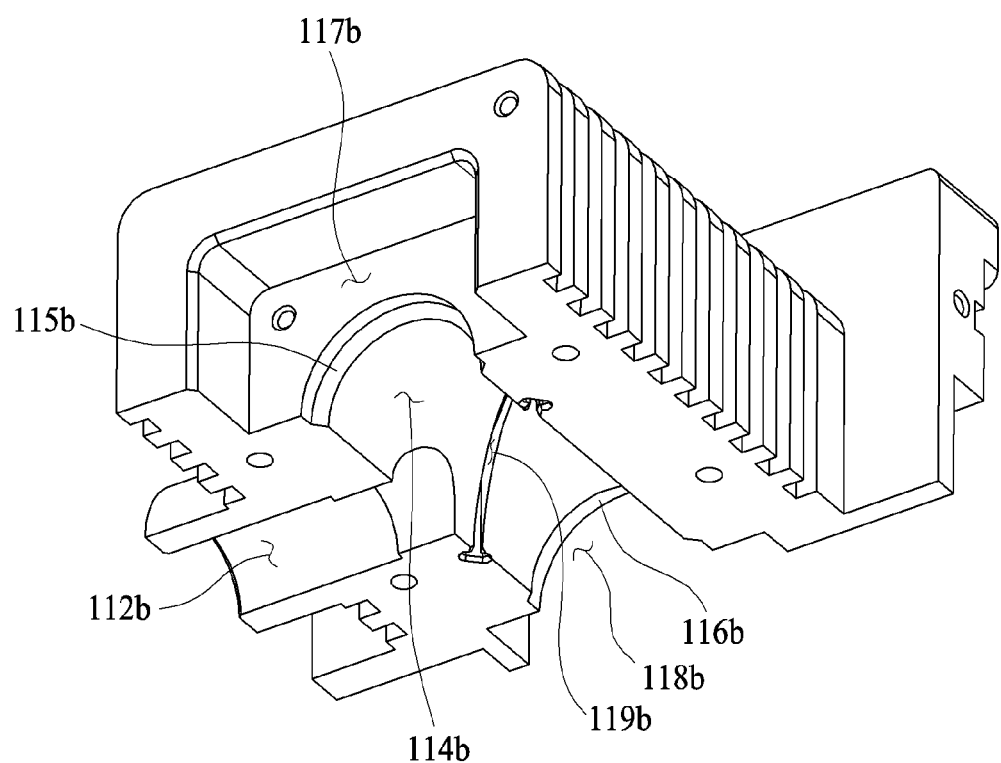

[Fig. 7]
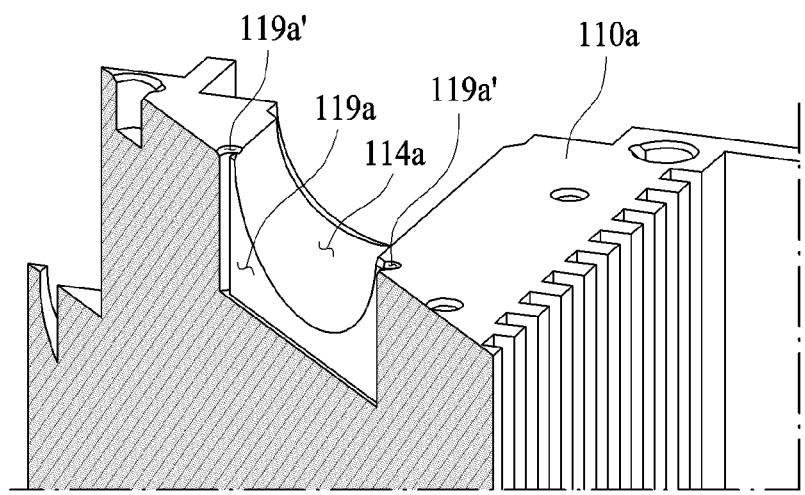

[Fig. 8]
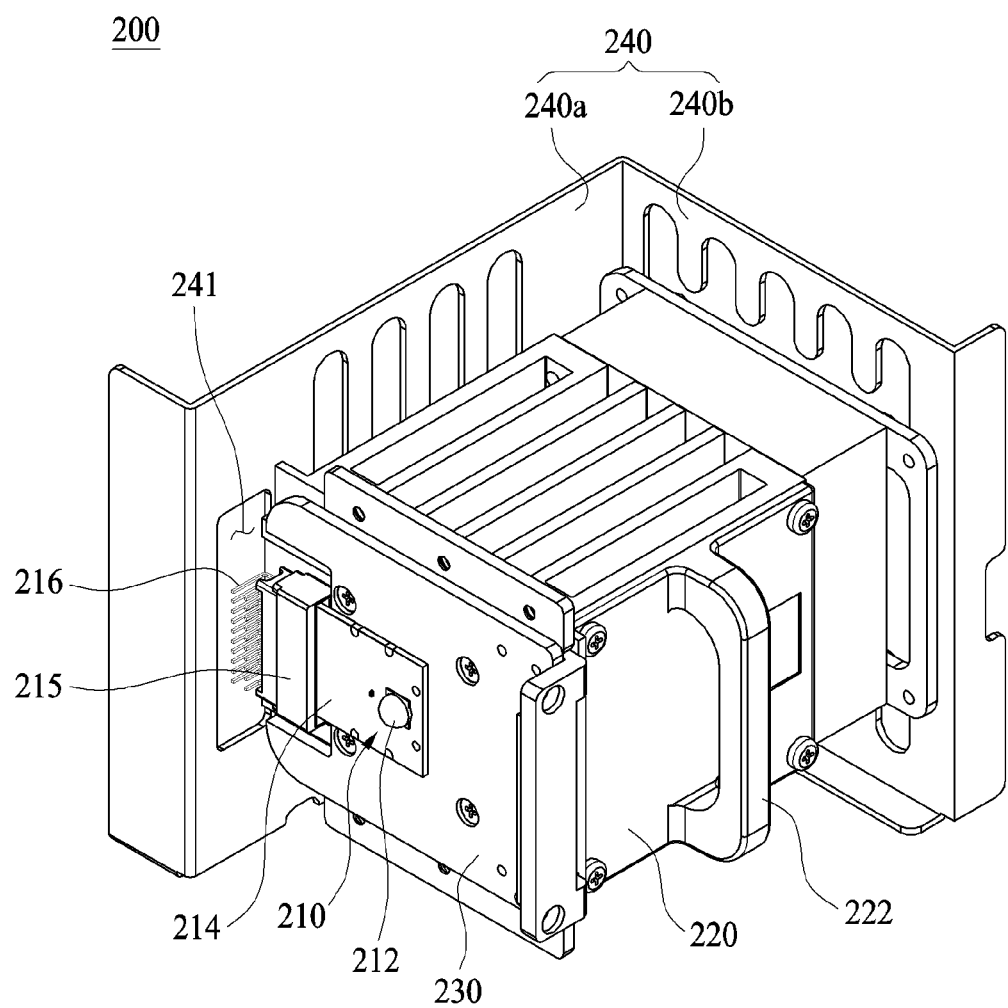

[Fig. 9]
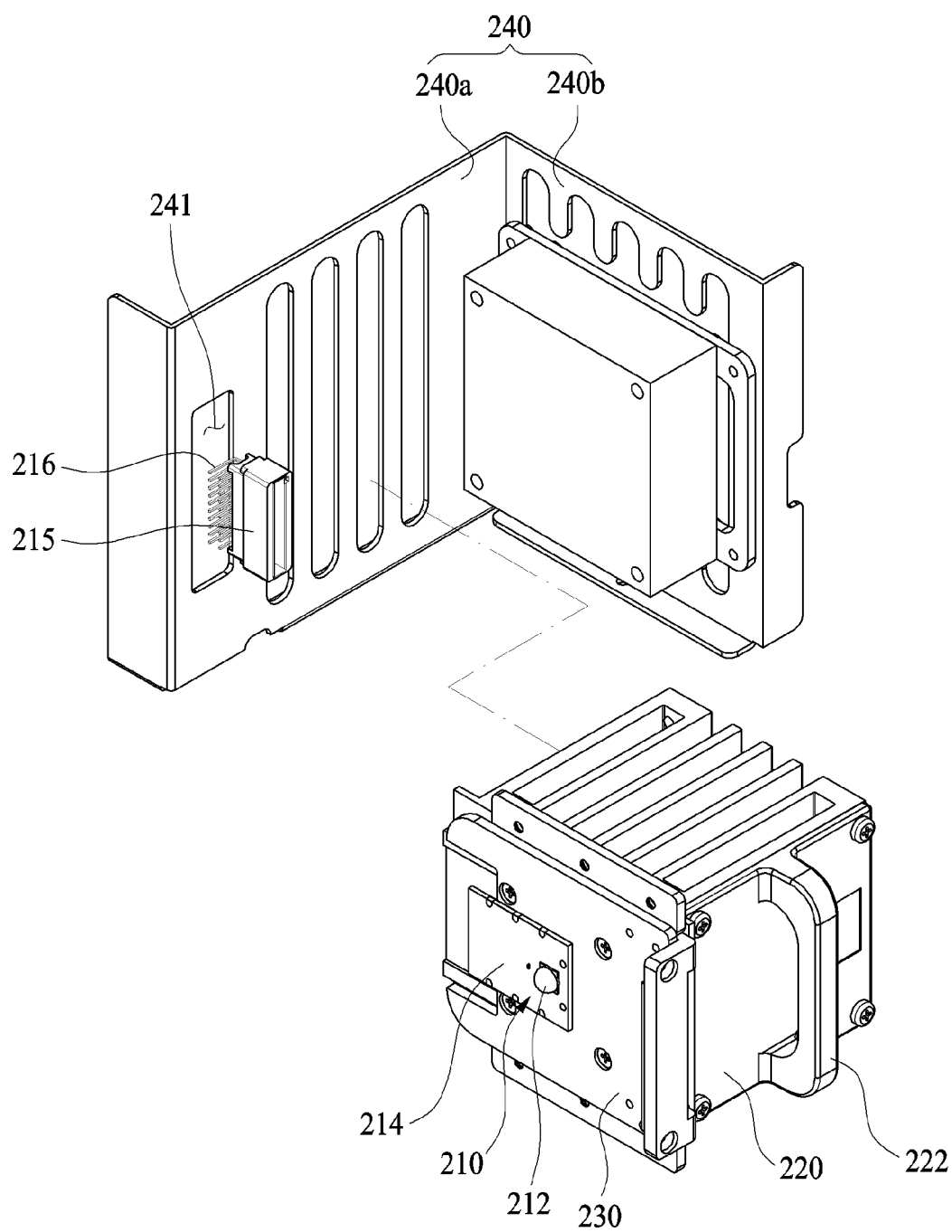

[Fig. 10]
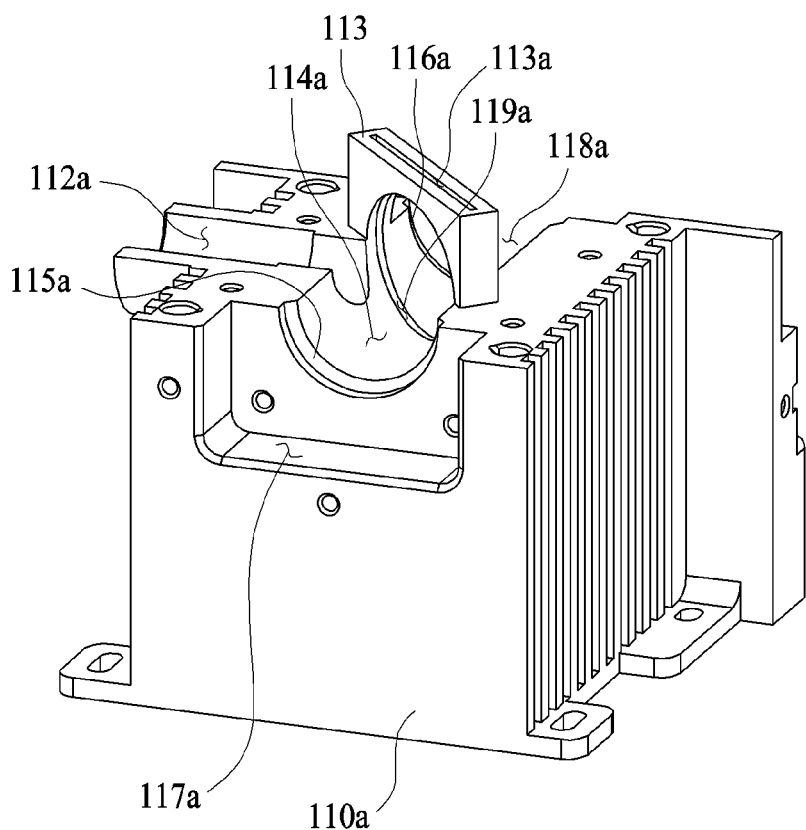

[Fig. 11]
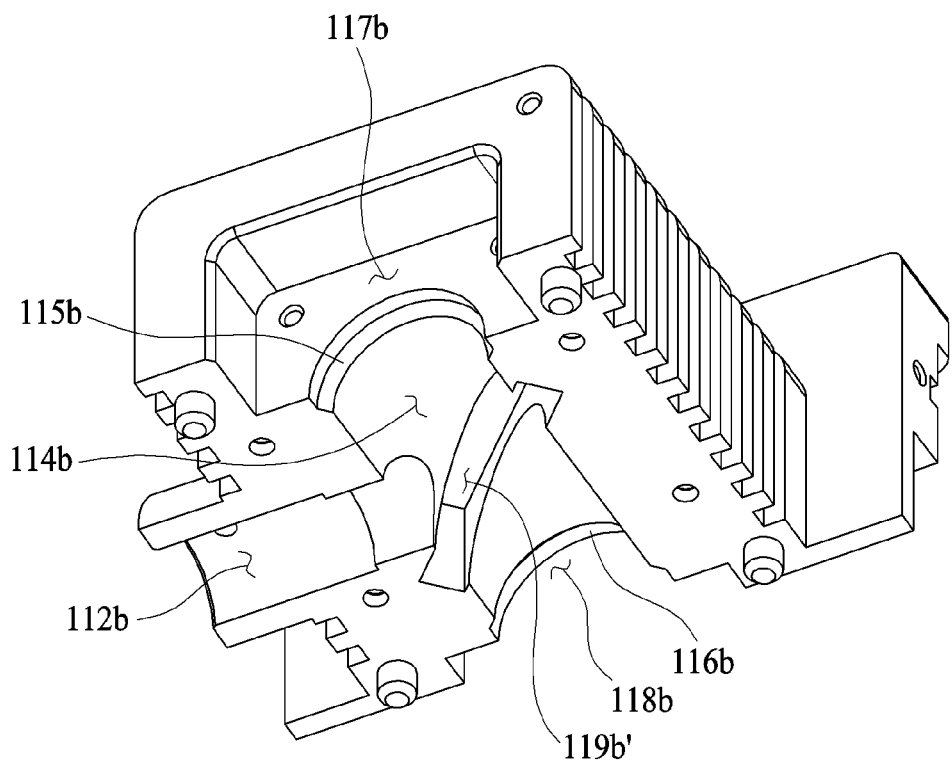

[Fig. 12]
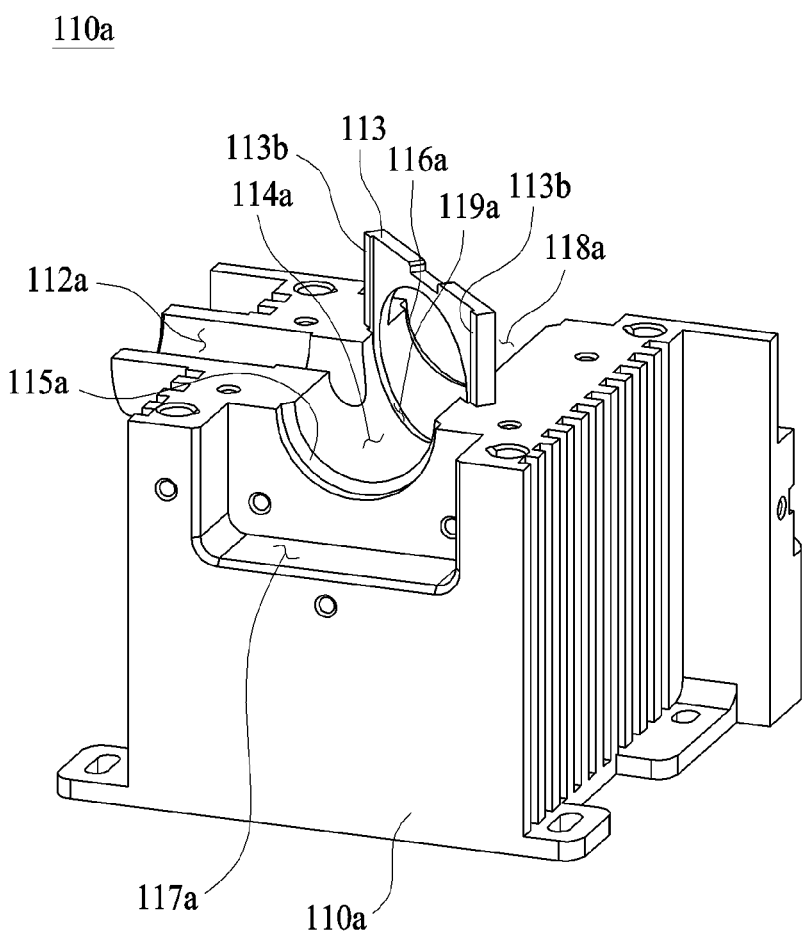

[Fig. 13]
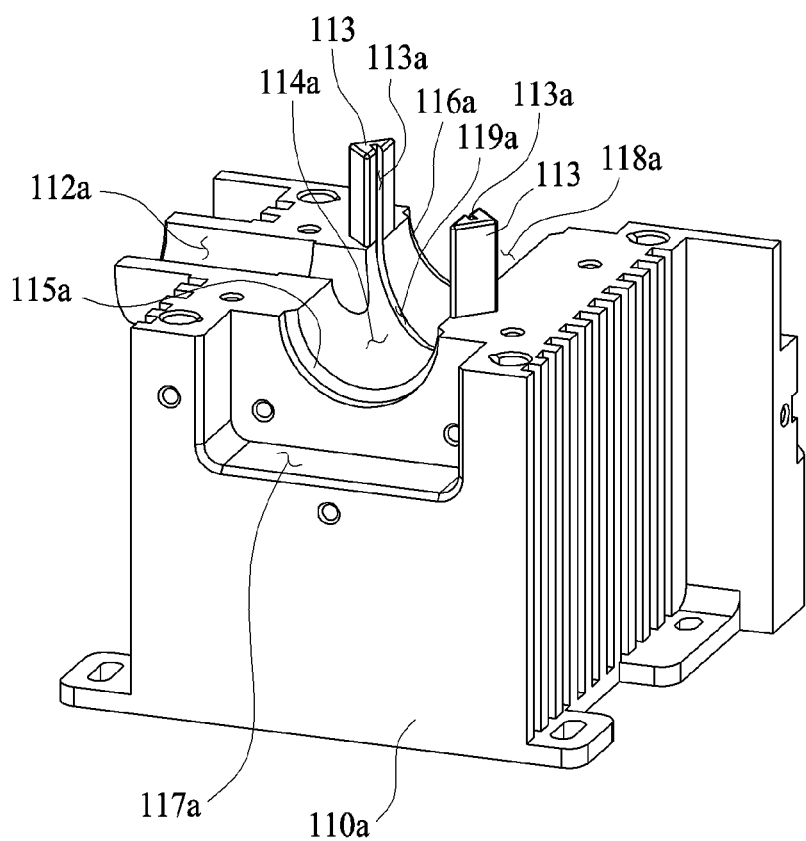

OPTIC ASSEMBLY AND LIGHT SOURCE DEVICE FOR ENDOSCOPE INCLUDING THE SAME

CROSS-REFERENCE TO RELATED APPLICATIONS

This application claims priority under 35 U.S.C. § 119 from Korean Application No. 10-2017-0053980 filed on Apr. 26, 2017, the subject matter of which is incorporated herein by reference.

BACKGROUND OF THE INVENTION

Field of the Invention

The present invention relates to an optical assembly and a light source device for endoscope including the same, and more particularly, to an optical assembly for changing a light irradiated from a first light source and a light irradiated from a second light source in a different direction from the first light source to be directed in the same direction, and a light source device for endoscope including the optical assembly.

Description of the Related Art

An endoscope is a device that can capture an image and observe narrow spaces such as the inside of a human body and the inside of a machine. It can be used not only in a medical field, but also in various industrial fields such as observing the inside of a precision machine without disassembling and observing abnormality in the inside of a pipe.

Particularly, in the medical field, the endoscope can observe the inside of a human body (stomach, bronchus, esophagus, large intestine, small intestine, etc.) by using a small-sized camera without the ventrotomy or incision of body such as surgery or autopsy, or observe the abdominal cavity by passing through a part of body such that it can check whether any abnormal exists.

A well-known conventional endoscope system includes, in a fore-end of the endoscope, a light source device for irradiating light to view the internal organs of body or the inside surface of a machine, an image sensor for receiving a light signal which is irradiated from the light source device is reflected from the surface of internal organ of human body after being projected and converting the received light signal into an electrical signal (image signal), and a camera with a camera chip including an encoder for converting the image signal into an electronic signal so that the image signal can be observed through a monitor.

Meanwhile, with the development of medical technology, an endoscopy through near-infrared rays as well as endoscopy through visible light is often performed. However, in the conventional case, since two types of light can not be simultaneously transmitted through a single endoscope, a separate check-up had to be carried out to accomplish two types of endoscopy.

This increases the time required for the operation, and further requires an additional effort by the operator and additional treatment costs, which also causes a patient to suffer pain due to repetitive procedures.

Accordingly, a method for solving such problems is required.

SUMMARY OF THE INVENTION

The present invention has been made in view of the above problems, and provides an optical assembly capable of simultaneously accomplishing multiple check-ups by transmitting a plurality of types of light through a single endoscope, and a light source device for endoscope including the optical assembly.

Thus, it is possible to reduce the time required for the operation and the cost of the operation, and to minimize the effort and suffering of patient and operator.

In accordance with an aspect of the present invention, an optical assembly includes: an upper case which is provided with a first optical path, formed therein, which passes light irradiated from a first light source, and a second optical path, formed therein, which communicates with a side of the first optical path and which introduces the light irradiated from a second light source in a direction different from the first light source into the first optical path; a lower case which is formed to correspond to the upper case and which is coupled with the upper case; and a beam splitter which is provided in the first optical path, and which maintains a traveling direction with respect to the light irradiated from the first light source and changes a direction of the light irradiated from the second light source so that the light irradiated from the second light source can travel in the same direction as the light irradiated from the first light source.

Each of the upper case and the lower case includes a first lens coupling unit which is formed in a front end of the first optical path and a second lens coupling unit which is formed in a rear end of the first optical path, and the optical assembly further includes a first lens which is coupled to the first lens coupling unit and a second lens which is coupled to the second lens coupling unit.

The optical assembly further includes a first shielding block which is coupled to the upper case and the lower case so as to shield a front of the first lens coupling unit and a second shielding block which is coupled to the upper case and the lower case so as to shield a rear of the second lens coupling unit.

An insertion groove corresponding to a cross-sectional shape of the beam splitter is formed on an inner circumferential surface of the first optical path formed in the upper case and the lower case, so that the beam splitter is inserted and fixed to the insertion groove.

The lower case is provided with an insertion groove, corresponding to a cross-sectional shape of the beam splitter, formed on an inner circumferential surface of the first optical path and a guide unit which protrudes to an upper portion of the lower case so that the beam splitter can be inserted into the insertion groove, and wherein the upper case is provided with a guide groove so that a guide unit of the lower case can be inserted into the upper case.

The guide unit is provided with a communication groove which communicates with the insertion groove of the lower case, wherein the beam splitter is slid along the communication groove of the guide unit to be inserted into the insertion groove of the lower case.

In accordance with another aspect of the present invention, a light source device for endoscope includes: an optical assembly comprising an upper case which is provided with a first optical path, formed therein, which passes light irradiated from a first light source, and a second optical path, formed therein, which communicates with a side of the first optical path and which introduces the light irradiated from a second light source in a direction different from the first light source into the first optical path; a lower case which is formed to correspond to the upper case and which is coupled with the upper case; and a beam splitter which is provided in the first optical path, and which maintains a traveling direction with respect to the light irradiated from the first light source and changes a direction of the light irradiated from the second light source so that the light irradiated from the second light source can travel in the same direction as the light irradiated from the first light source; and a first light source assembly which is disposed in a rear of the optical assembly and which is provided with an optical element for irradiating light to the first optical path.

The first light source assembly includes: a substrate which is provided with the optical element; a cooling module which comes in contact with a rear of the substrate to perform cooling; and a fixing frame which fix the substrate and the cooling module.

The fixed frame includes a rear shielding unit which shields a rear of the cooling module and a side shielding unit which shields one side.

The substrate and the cooling module are detachable from the fixing frame in an opposite direction. The side shielding unit is provided with a withdrawal hole which allows a connector connected to the substrate to be drawn out to one side.

BRIEF DESCRIPTION OF THE DRAWINGS

The objects, features and advantages of the present invention will be more apparent from the following detailed description in conjunction with the accompanying drawings, in which:

FIG. 1 is a diagram illustrating a schematic configuration of an endoscope system according to the present invention;

FIG. 2 is a diagram illustrating an internal structure of a light source device applied to an endoscope system of the present invention;

FIG. 3 is a diagram illustrating a light source device applied to an endoscope system according to a first embodiment of the present invention;

FIG. 4 is a diagram illustrating a structure of an optical assembly in a light source device applied to an endoscope system according to a first embodiment of the present invention;

FIG. 5 is a diagram illustrating a lower case of an optical assembly in a light source device applied to an endoscope system according to a first embodiment of the present invention;

FIG. 6 is a diagram illustrating a lower case of an optical assembly in a light source device applied to an endoscope system according to a first embodiment of the present invention;

FIG. 7 is a diagram illustrating a structure of an insertion groove in a light source device applied to an endoscope system according to a first embodiment of the present invention;

FIG. 8 is a diagram illustrating a structure of a first light source assembly in a light source device applied to an endoscope system according to a first embodiment of the present invention;

FIG. 9 is a diagram illustrating a separation structure of a cooling module in a light source device applied to an endoscope system according to a first embodiment of the present invention;

FIG. 10 is a diagram illustrating a lower case of an optical assembly in a light source device applied to an endoscope system according to a second embodiment of the present invention;

FIG. 11 is a diagram illustrating an upper case of an optical assembly in a light source device applied to an endoscope system according to a second embodiment of the present invention;

FIG. 12 is a diagram illustrating a lower case of an optical assembly in a light source device applied to an endoscope system according to a third embodiment of the present invention; and FIG. 13 is a diagram illustrating a lower case of an optical assembly in a light source device applied to an endoscope system according to a fourth embodiment of the present invention.

DETAILED DESCRIPTION OF EXEMPLARY EMBODIMENTS

Exemplary embodiments of the present invention are described with reference to the accompanying drawings in detail. The same reference numbers are used throughout the drawings to refer to the same or like parts. Detailed descriptions of well-known functions and structures incorporated herein may be omitted to avoid obscuring the subject matter of the present invention.

FIG. 1 is a diagram illustrating a schematic configuration of an endoscope system according to the present invention.

Referring to FIG. 1, the endoscope system according to a first embodiment of the present invention may include a light source device 500, an image processing device 50, an electronic endoscope 30 (hereinafter, referred to as an endoscope 30), an image display device 70, and an input device (not shown).

The light source device 500 may be provided with a combined white-NIR illuminator including a first light source assembly 200 and a second light source assembly 300 to obtain information such as biological characteristics from an object (e.g., the internal organs of the human body) to be observed, and transmit a light irradiated from them to the endoscope 30. In the present embodiment, it is assumed that the first light source assembly 200 irradiates a white light and the second light source assembly 300 irradiates a near-infrared ray. However, the light irradiated from the first light source assembly 200 and the second light source assembly 300 is not limited thereto.

The image processing device 50 may control an image processing of the endoscope 30 and perform an image signal processing on an image obtained by the endoscope 30.

The endoscope 30 may be electrically detachably connected to the image processing device 50, and may be optically coupled to the light source device 500 through an optical cable. The white light or the near infrared ray excitation light transmitted from the light source device 500 may be irradiated to the inside of human body, and the visible light reflected from an object, the near infrared ray excitation light, and the fluorescence caused by the near infrared ray excitation light may be observed as an image by a built-in image sensor. At this time, the image sensor may convert the captured image into an image signal.

The image display device 70 and the input device may be connected to the image processing device 50. The image display device 70 may be implemented of an LCD capable of displaying the generated image or any other form capable of displaying an image as such. The input device may include a form capable of inputting various types of information to the image processing device 50 or the image display device 70 such as an input button provided in the endoscope 30, or a keyboard or a mouse which is separately provided.

The endoscope 30 capable of observing the visible light irradiated from an observation target or the light in a near infrared ray excitation light region may include a flexible or rigid insertion unit 30a inserted into a body cavity in which light hardly reaches, an operation unit 30b provided at the end of the insertion unit 30a, and a universal cord unit 30c extending from the side of the operation unit 30b, and electrically connected to the image processing device 50 through the universal cord unit 30c.

A main body unit of the endoscope 30 may mainly include the insertion unit 30a and the operation unit 30b, and the captured image signal and control signals may be transmitted to the image processing device 50 through a cable 3a.

An image sensor 3 such as CMOS or CCD, an air/water channel and a forceps hole may be provided in a distal end of the insertion unit 30a. Since the forces hole is well known to those skilled in the art, a detailed description is omitted.

The image sensor 3 may be electrically connected to an image sensor driver 52 through the cable 3a bundled with a plurality of signal wires.

A light guide 15 may be connected to the light source unit 500 through the universal cord unit 30c in the insertion unit 30a. The light guide 15 may include an optical system (not shown), and may guide a compound light source provided to the light source device 500, i.e., a white light source and a near infrared ray excitation light to be output to the end of the insertion unit.

The image processing device 50 may include an image sensor controller 54, an image sensor driver 52, a gain amplifier 62, an analog-to-digital converter (ADC) 64, a digital signal processor (DSP) 66, and a digital-to-analog converter (DAC) 68.

The image sensor driving unit 52 may drive an image sensor 1 built in the endoscope 30, and may be controlled in such a manner that a control input through the image sensor controller 54 is processed by a CPU 60.

The gain amplifier 62 may perform gain control for the image signal generated by the image sensor 1, and the analog-to-digital converter 64 may convert the image signal into a digital signal.

The digital signal processor 66 may perform various types of image processing such as image synthesis and white balancing for the digital image signal.

In addition, the digital signal processor 66 may adjust the image processing timing in cooperation with the CPU 60.

The digital-to-analog converter 68 may perform a process for displaying image data, for example, an analog process, and output the image data to the image display device 70.

The light source device 500 connected to the light guide 15 may include an optical assembly (Optical Coupler) 100, the second light source assembly (NIR-LD) 300, the first light source assembly (White-LED) 200, and a light source controller 400. A detailed structure of the light source device 500 is described with reference to FIG. 2.

FIG. 2 is a diagram illustrating an internal structure of the light source device 500 applied to an endoscope system of the present invention.

As described above, the light source device 500 may include the optical assembly 100, the first light source assembly 200, the second light source assembly 300, and the light source controller 400.

These elements may be housed in a housing of the light source device 500. On the inner side of the rear panel of the housing, at least one cooling fan 82 may be disposed to dissipate a heat generated in the components in the housing, and an adapter 84 plugged for the application of an external alternating current (AC) power may be disposed.

A direct current power supply 80 may be disposed inside the housing to be adjacent to the adapter 84 and convert the alternating current (AC) power applied to the adapter 84 into a direct current (DC) power.

The optical assembly 100 is an element which collects optical signals transmitted from the first light source assembly 200 and the second light source assembly 300 and transmits the collected optical signals to the endoscope side. Here, the first light source assembly 200 and the second light source assembly 300 may be controlled by the light source controller 400.

In addition, as described above, in the present embodiment, it is assumed that the first light source assembly 200 irradiates a white light and the second light source assembly 300 irradiates a near infrared ray. However, the light irradiated from the first light source assembly 200 and the second light source assembly 300 is not limited thereto.

Meanwhile, the light source device 500 according to the embodiment of the present invention may include an electrostatic touch assembly 70 for controlling each light source through an operation. The electrostatic touch assembly 70 may perform quick and accurate input by applying an electrostatic touch method, and may prevent a malfunction and a breakdown due to various electric outbreak situations fundamentally. In addition, the light source control method of the light source device is not limited to the electrostatic touch method, and any method for controlling the light source can be applied.

Hereinafter, the optical assembly 100, the first light source assembly 200, and the second light source assembly 300 are described in detail.

FIG. 3 is a diagram illustrating the optical assembly 100 and the first light source assembly 200 applied to an endoscope system according to a first embodiment of the present invention.

As shown in FIG. 3, in the present embodiment, the optical assembly 100 may include a case 110 divided into an upper case 110b and a lower case 110a, and the first light source assembly 200 may be provided in the rear side of the optical assembly 100. It is preferable that the optical assembly 100 may be divided into upper and lower cases 110b and 110a for the convenience of an internal optical system or a mechanical assembly. However, it may be configured of a single unit assembly having a structure in which an optical system can be inserted therein.

The first light source assembly 200 may include a cooling module 220 formed in a form of a heat sink, a first light source 210 (see FIG. 8) provided with an optical element 212 (see FIG. 8) cooled by the cooling module 220 and a substrate 214 (see FIG. 8), and a fixing frame 240 for supporting the first light source 210 and the cooling module 220.

A light transmitting unit 310 for transmitting light from the second light source assembly 300 (see FIG. 2) may be connected to the side of the optical assembly 100.

Hereinafter, the optical assembly 100 is described in detail, and then the structure of the first light source assembly 200 is described.

FIG. 4 is a diagram illustrating a structure of the optical assembly 100 in a light source device applied to an endoscope system according to a first embodiment of the present invention. FIG. 5 is a diagram illustrating the lower case 110a of the optical assembly 100 in a light source device applied to an endoscope system according to a first embodiment of the present invention, and FIG. 6 is a diagram illustrating the upper case 110b of the optical assembly 100 in a light source device applied to an endoscope system according to a first embodiment of the present invention.

As shown in FIGS. 4 to 6, the optical assembly 100 may include the case 110, a beam splitter 150 coupled to the inside of the case 110, a first lens 120, a second lens 125, a first shielding block 130, and a second shielding block 140.

A first optical path 114a and 114b which passes the light irradiated from the first light source, and a second optical path 112a and 112b which communicates with the side of the first optical path 114a and 114b and which introduces the light irradiated from the second light source in the direction different from the first light source into the first optical path 114a and 114b may be formed in the inside of the case 110.

In addition, as described above, in the present embodiment, the case 110 may include the upper case 110b and the lower case 110a which are formed so as to divide the first optical path 114a and 114b and the second optical path 112a and 112b formed inside the case 110 into two parts.

The first optical path 114a and 114b may form a path for passing the light irradiated from the first light source of the first light source assembly 200 (see FIG. 3) provided in the rear side of the optical assembly 100. In the present embodiment, the first optical path 114a and 114b may be formed to extend linearly from the rear side of the case 110 to the front side.

In addition, the second optical path 112a and 112b may be extended in the vertical direction from the middle point of the first optical path 114a and 114b, and may form a path for passing the light irradiated from the second light source of the second light source assembly 300 (see FIG. 2) provided in one side of the optical assembly 100. That is, the light irradiated through the second optical path 112a and 112b may reach a confluence point of the first optical path 114a and 114b and the second optical path 112a and 112b.

At this time, the beam splitter 150 may be provided adjacent to the first optical path 114a and 114b, specifically, the confluence point of the first optical path 114a and 114b and the second optical path 112a and 112b.

The beam splitter 150 may maintain the traveling direction with respect to the light irradiated from the first light source, and may change the direction of the light irradiated from the second light source so that the light irradiated from the second light source travels in the same direction as the light irradiated from the first light source. That is, the light irradiated from the first light source and the light irradiated from the second light source may be irradiated from a different direction. However, they may be diverted to the same direction by the beam splitter 150 and transmitted to the endoscope side.

As the beam splitter 150, a dichronic mirror or the like may be applied, and in addition, various optical mirrors may be used.

Particularly, in the present embodiment, an insertion groove 119a and 119b, corresponding to a cross-sectional shape of the beam splitter 150, may be formed on the inner circumferential surface of the first optical path 114a and 114b so that the beam splitter 150 may be inserted and fixed to the insertion groove.

The insertion groove 119a and 119b may be formed adjacent to the confluence point of the first optical path 114a and 114b and the second optical path 112a and 112b and the first optical path 114a and 114b, and may be formed in an oblique direction with respect to each of the first optical path 114a and 114b and the second optical path 112a and 112b to fix the beam splitter 150.

In addition, in the present embodiment, the case 110 may include a first lens coupling unit 115a and 115b which is formed in the front end of the first optical path 114a and 114b, and a second lens coupling unit 116a and 116b which is formed in the rear end of the first optical path 114a and 114b. Thus, a first lens 120 may be coupled to the first lens coupling unit 115a and 115b, and a second lens 125 may be coupled to the second lens coupling unit 116a and 116b.

The first lens 120 and the second lens 125 may determine the transmittance of light according to the optical characteristic. In the present embodiment, the first lens 120 and the second lens 125 may be formed in such a manner that one surface is flat and the other surface is manufactured in a protruding shape, and the other surface faces toward the beam splitter 150 side. At this time, the first lens coupling unit 115a and 115b and the second lens coupling unit 116a and 116b may have a step corresponding to a circumference surface shape of the first lens 120 and the second lens 125 so that the first lens 120 and the second lens 125 may be stably mounted.

In addition, in the present embodiment, the optical assembly 100 may further include a first shielding block 130 coupled to the case 110 so as to shield the front of the first lens coupling unit 115a and 115b, and a second shielding block 140 coupled to the case 110 so as to shield the rear of the second lens coupling unit 116a and 116b.

The first shielding block 130 and the second shielding block 140 may prevent the first lens 120 and the second lens 125 from being detached to the outside of the case 110. In detail, a first shielding block 130 may be fastened to a first block coupling unit 117a and 117b formed in the front end of the case 110, and a second shielding block 140 may be fastened to a second block coupling unit 118a and 118b formed in the rear end of the case 110.

The first shielding block 130 and the second shielding block 140 may be provided with through holes 131 and 141 through which light can pass respectively. The diameter of the through holes 131 and 141 may be formed smaller than the first lens 125 and the second lens 125. This is to prevent the first lens 120 and the second lens 125 from being detached through the through holes 131 and 141.

Meanwhile, in the case of the second shielding block 140, as shown in the drawing, the border surface may have a concavo-convex shape to effectively dissipate the heat generated in the light source.

FIG. 7 is a diagram illustrating a structure of an insertion groove 119a and 119b in a light source device applied to an endoscope system according to a first embodiment of the present invention.

As shown in FIG. 7, the insertion groove 119a and 119b may be formed in an oblique shape on the first optical path 114a and have a cross section corresponding to the shape of the beam splitter 150.

In addition, in the present embodiment, since the beam splitter 150 is formed in a rectangular shape, the insertion groove 119a and 119b is also formed in a rectangular shape having a size corresponding to the beam splitter 150 in a state where the upper case 110b and the lower case 110a may be coupled to each other. The shape of the beam splitter 150 and the shape of the insertion groove 119a and 119b which is formed such that the upper case 110b and the lower case 110a are coupled to each other are not limited to a specific shape, and can be implemented in any form in order to enhance assemblability or function.

Thus, the lower portion of the beam splitter 150 may be inserted into the insertion groove 119a of the lower case 110a while the upper case 110b and the lower case 110a are separated from each other. Then, the insertion groove 119a of the upper case 110b may be fitted into the upper portion of the beam splitter 150 such that the upper case 110b and the lower case 110a may be coupled to each other.

As described above, according to the present invention, the beam splitter 150 can be easily combined and separated as the case 110 is divided into the upper case 110b and the lower case 110a, which is advantageous for maintenance and replacement.

On the other hand, in the present embodiment, an auxiliary groove 119a' protruding in the thickness direction of the insertion groove 119a and 119b may be formed in both ends of the insertion groove 119a and 119b, so that the beam splitter 150 can be easily inserted.

In addition, when an auxiliary guide (not shown) having a corresponding shape is formed in both ends of the beam splitter 150 so as to be inserted into the auxiliary groove 119a', the beam splitter 150 can be fixed to the insertion groove 119a and 119b more stably without shaking.

Next, the structure of the first light source assembly 200 is described.

FIG. 8 is a diagram illustrating a structure of the first light source assembly 200 in a light source device applied to an endoscope system according to a first embodiment of the present invention, and FIG. 9 is a diagram illustrating a separation structure of a cooling module 220 in a light source device applied to an endoscope system according to a first embodiment of the present invention.

As shown in FIGS. 8 and 9, the first light source assembly 200 may include the first light source 210 including the optical element 212 and the substrate 214, the cooling module 220, and the fixing frame 240.

The optical element 212 may be provided in the rear side of the optical assembly 100 and irradiate a first light to the first optical path 114a and 114b, may be mounted on the substrate 214 formed to be detachable from a connector 215, and may be electrically connected to a driving power source installed in an interior via a cable 216.

In addition, since the substrate 214 may be severely heated, the cooling module 220 may be disposed on the rear side of the substrate 214 in a state where the cooling module 220 is in contact with the substrate 214. The cooling module 220 may be formed in the form of a cooling fin having a plurality of hollows formed therein. Particularly, a connection member 230 for directly contacting the substrate 214 may be provided between the cooling module 220 and the substrate 214.

The connection member 230 may be coupled to the cooling module 220, and may be formed of a material having excellent thermal conductivity so as to transfer the heat generated in the substrate 214 to the cooling module 220 rapidly.

In addition, the first light source 210 may be integrated with the connection member 230 or may be coupled to the connection member 230 by using a coupling member such as a bolt.

The fixing frame 240 may be an element that supports the entire of the first light source 210 including the substrate 214 and the cooling module 220. In the present embodiment, the fixing frame 240 may include a rear shielding unit 240b for shielding the rear of the cooling module 220 and a side shielding unit 240a for shielding one side. In this case, for convenience of explanation, the one side refers to the right side when viewed from the rear of the cooling module 220, and the other side refers to the left side when viewed from the rear of the cooling module 220.

That is, the fixing frame 240 may be coupled to the cooling module 220 by a bolt or the like to fix the cooling module 220. A plurality of holes may be formed on the surface of the fixing frame 240 so that the heat transferred from the first light source 210 cannot increase the temperature.

In addition, in the present embodiment, the cooling module 220, the connection member 230, and the first light source 210 may form a single unit structure so as to be detachable from the fixing frame 240 by sliding in the other direction. This is to facilitate the separation of the first light source 210 or the cooling module 220, thereby facilitating maintenance and replacement work. To this end, a handle unit 222 may be formed in the other side of the cooling module 220 so that a user can grip and take out the cooling module 220.

That is, when it is necessary to replace or repair the first light source 210 or the cooling module 220, the user can release the fastened state of the cooling module 220 and pull out it in the other direction by using the handle unit 222 while removing the first light source 210 from the connector 215.

On the other hand, the side shielding unit 240a of the fixing frame 240 may have a withdrawal hole 241 for allowing the substrate 214 to be drawn out to one side. This can be used for the connector 215 to be separated from the cooling module 220 in the opposite direction, when the maintenance and replacement of the connector 215 connected to the first light source 210 is required, as in the case of separating the cooling module 220 in the other direction.

The first embodiment of the present invention is described above, and other embodiments of the present invention are described below.

FIG. 10 is a diagram illustrating a lower case 110a of an optical assembly in a light source device applied to an endoscope system according to a second embodiment of the present invention, and FIG. 11 is a diagram illustrating an upper case 110b of an optical assembly in a light source device applied to an endoscope system according to the second embodiment of the present invention.

In the case of the optical assembly according to the second embodiment of the present invention shown in FIGS. 10 and 11, all elements may be the same as those of the first embodiment described above. However, the element for fixing the beam splitter 150 may be formed somewhat differently.

Specifically, in the present embodiment, the lower case 110a may be provided with a guide unit 113a which protrudes to an upper portion of the lower case 110a so as to be insertable into the upper case 110b, and which is provided with a communication groove 113a, formed on an inner side, for communicating with an insertion groove 119a of the lower case 110a.

The guide unit 113 allows the beam splitter 150 to be more easily inserted into the insertion groove 119a of the lower case 110a, and also serves to prevent the beam splitter 150 from being shaken or damaged by an external shock or the like in the state where the beam splitter 150 is inserted into the insertion groove 119a and 119b.

At this time, the guide groove 119b' of the upper case 110b may be formed to have a thickness corresponding to the guide unit 113 so that the guide unit 113 can be inserted.

FIG. 12 is a diagram illustrating a lower case 110a of an optical assembly in a light source device applied to an endoscope system according to a third embodiment of the present invention Like the second embodiment of the present invention, also in the third embodiment of the present invention shown in FIG. 12, the lower case 110a further includes the guide unit 113 protruding upward.

However, in the case of the guide unit 113 of the present embodiment, it is not formed in a shape in which a communication groove is formed on an inner side, but a guide stepped part 113b is formed at both ends of the guide unit 113. Therefore, the beam splitter 150 can be inserted into the insertion groove 119a of the lower case 110a while being seated in the front of the guide unit 113.

In addition, also in the present embodiment, the insertion groove 119b of the upper case 110b may be formed to have a thickness corresponding to the guide unit 113 so that the guide unit 113 can be inserted.

FIG. 13 is a diagram illustrating a lower case 110a of an optical assembly in a light source device applied to an endoscope system according to a fourth embodiment of the present invention.

Like the second and third embodiments of the present invention, also in the fourth embodiment of the present invention shown in FIG. 13, the lower case 110a further includes the guide unit 113 protruding upward.

However, in the case of the guide unit 113 of the present embodiment, the guide units 113 may be formed in pairs and each of the guide units may be implemented in a standing position from both ends of the insertion groove 119a of the lower case 110a. In addition, the communication groove 113a for communicating with the insertion groove 119a of the lower case 110a may be formed on an inner side of the pair of guide unit.

Accordingly, the beam splitter 150 can be stably inserted between the pair of guide units 113.

In addition, also in the present embodiment, both ends of the insertion groove 119b of the upper case 110b may be formed to have a thickness corresponding to the guide unit 113 so that the pair of guide units 113 can be inserted.

According to the present invention, the advantages of the optical assembly and the light source device for endoscope including the optical assembly are as follows.

First, as the light source device for endoscope of the present invention is provided, various types of light can be transmitted through a single endoscope, so that a complex check-up can be performed simultaneously.

Second, the time required for operation and the cost of operation can be significantly reduced.

Third, the effort of operator and the suffering of patient can be minimized.

Fourth, since each element can be easily separated from each other, the effort required for maintenance can be minimized.

Hereinabove, although the present invention has been described with reference to exemplary embodiments and the accompanying drawings, the present invention is not limited thereto, but may be variously modified and altered by those skilled in the art to which the present invention pertains without departing from the spirit and scope of the present invention claimed in the following claims.

What is claimed is:

1. An optical assembly comprising:
   an upper case which is provided with a first optical path, formed therein, which passes light irradiated from a first light source, and a second optical path, formed therein, which communicates with a side of the first optical path and which introduces the light irradiated from a second light source in a direction different from the first light source into the first optical path;
   a lower case which is formed to correspond to the upper case and which is coupled with the upper case; and
   a beam splitter which is provided in the first optical path, and which maintains a traveling direction with respect to the light irradiated from the first light source and changes a direction of the light irradiated from the second light source so that the light irradiated from the second light source can travel in the same direction as the light irradiated from the first light source,
   wherein each of the upper case and the lower case comprises a first lens coupling unit which is formed in a front end of the first optical path and a second lens coupling unit which is formed in a rear end of the first optical path,
   wherein a first lens and a second lens are coupled to the first lens coupling unit and the second lens coupling unit, respectively,
   wherein a first shielding block is coupled to the upper case and the lower case so as to shield a front of the first lens coupling unit and a second shielding block is coupled to the upper case and the lower case so as to shield a rear of the second lens coupling unit.

2. The optical assembly of claim 1, wherein an insertion groove corresponding to a cross-sectional shape of the beam splitter is formed on an inner circumferential surface of the first optical path formed in the upper case and the lower case, so that the beam splitter is inserted and fixed to the insertion groove.

3. The optical assembly of claim 1, wherein the lower case is provided with an insertion groove, corresponding to a cross-sectional shape of the beam splitter, formed on an inner circumferential surface of the first optical path and a guide unit which protrudes to an upper portion of the lower case so that the beam splitter can be inserted into the insertion groove, and
   wherein the upper case is provided with a guide groove so that a guide unit of the lower case can be inserted into the upper case.

4. The optical assembly of claim 3, wherein the guide unit is provided with a communication groove which communicates with the insertion groove of the lower case,
   wherein the beam splitter is slid along the communication groove of the guide unit to be inserted into the insertion groove of the lower case.

5. A light source device for endoscope, the device comprising:
   an optical assembly comprising an upper case which is provided with a first optical path, formed therein, which passes light irradiated from a first light source, and a second optical path, formed therein, which communicates with a side of the first optical path and which introduces the light irradiated from a second light source in a direction different from the first light source into the first optical path; a lower case which is formed to correspond to the upper case and which is coupled with the upper case; and a beam splitter which is provided in the first optical path, and which maintains a traveling direction with respect to the light irradiated from the first light source and changes a direction of the light irradiated from the second light source so that the light irradiated from the second light source can travel in the same direction as the light irradiated from the first light source; and
   a first light source assembly which is disposed in a rear of the optical assembly and which is provided with an optical element for irradiating light to the first optical path,
   wherein the first light source assembly comprises a substrate which is provided with the optical element, a cooling module which comes in contact with a rear of the substrate to perform cooling, and a frame which fixes together the substrate and the cooling module,
   wherein the frame comprises a rear shielding unit which shields a rear of the cooling module and a side shielding unit which shields one side of the cooling module, having a withdrawal hole which allows a connector connected to the substrate to be drawn out to one side of the frame.

6. The device of claim 5, wherein the substrate and the cooling module are detachable from the frame in an opposite direction.

* * * * *